(12) United States Patent
Schmid et al.

(10) Patent No.: US 8,715,629 B2
(45) Date of Patent: May 6, 2014

(54) COSMETIC OLIGO-α-OLEFIN CONTAINING COMPOUND

(75) Inventors: Karl Heinz Schmid, Mettmann (DE); Alfred Westfechtel, Hilden (DE); Achim Ansmann, Erkrath (DE); Markus Dierker, Duesseldorf (DE); Stefan Bruening, Philadelphia, PA (US)

(73) Assignee: Cognis IP Management GmbH, Duesseldorf (DE)

(*) Notice: Subject to any disclaimer, the term of this patent is extended or adjusted under 35 U.S.C. 154(b) by 2092 days.

(21) Appl. No.: 10/553,165

(22) PCT Filed: Apr. 7, 2004

(86) PCT No.: PCT/EP2004/003693
§ 371 (c)(1), (2), (4) Date: Aug. 4, 2006

(87) PCT Pub. No.: WO2004/091555
PCT Pub. Date: Oct. 28, 2004

(65) Prior Publication Data
US 2007/0081959 A1    Apr. 12, 2007

(30) Foreign Application Priority Data

Apr. 16, 2003 (DE) .................................. 103 17 781
May 28, 2003 (DE) .................................. 103 24 508
Aug. 7, 2003 (DE) .................................. 103 36 172

(51) Int. Cl.
*A61Q 15/00* (2006.01)
*A61Q 19/00* (2006.01)

(52) U.S. Cl.
USPC .................. 424/65; 424/47; 424/59; 424/401

(58) Field of Classification Search
None
See application file for complete search history.

(56) References Cited

U.S. PATENT DOCUMENTS

| | | | |
|---|---|---|---|
| 3,806,470 A * | 4/1974 | Aykan et al. .................. 502/311 |
| 3,954,897 A | 5/1976 | Yamato et al. | |
| 4,152,490 A | 5/1979 | Witzke | |
| 4,339,344 A | 7/1982 | Boden et al. | |
| 4,919,934 A * | 4/1990 | Deckner et al. ............... 424/401 |
| 5,068,490 A | 11/1991 | Eaton | |
| 5,286,823 A | 2/1994 | Rath | |
| 5,633,420 A * | 5/1997 | Theriot et al. ................. 585/525 |
| 5,833,963 A * | 11/1998 | Mackles et al. ................. 424/65 |
| 6,133,209 A * | 10/2000 | Rath et al. ..................... 508/448 |
| 6,403,070 B1 | 6/2002 | Pataut et al. | |
| 6,464,967 B1 * | 10/2002 | Collin .......................... 424/70.7 |
| 2001/0034461 A1 | 10/2001 | Connor | |
| 2004/0267073 A1 | 12/2004 | Zander et al. | |

FOREIGN PATENT DOCUMENTS

| | | |
|---|---|---|
| DE | 2360306 | 7/1974 |
| DE | 27 026 04 | 8/1984 |
| EP | 0337737 | 10/1989 |
| EP | 575 356 | 12/1993 |
| EP | 1 103 249 | 5/2001 |
| EP | 1 232 739 | 8/2002 |
| WO | WO 85/01942 | 5/1985 |
| WO | WO 98/20053 | 5/1998 |
| WO | 01/00151 | 1/2001 |
| WO | 03/028678 | 4/2003 |
| WO | PCT/EP02/11392 | 5/2003 |

OTHER PUBLICATIONS

U. Zeidler, "Über das Spreiten von Lipiden auf der Haut", Fette, Seifen, Anstrichmittel, vol. 87, 1985, pp. 403-408.
Chauvel et al., "Petrochemical Processes", vol. 1, Editions Technip, 1989, pp. 183-187.
F. Nierlich, "Oligomerize for better gasoline", Hydrocarbon Processing, Feb. 1992, pp. 45-46.
Kosmetikverordnung, Deutsches Institut für Körperpflege und Hygiene e.V., Appendix 6, Parts A and B.

* cited by examiner

Primary Examiner — Jyothsna Venkat
(74) Attorney, Agent, or Firm — Servilla Whitney LLC

(57) ABSTRACT

The disclosed invention relates to a cosmetic composition containing at least one branched oligo-α-olefin, characterized in that the side chains at one branch point at least are ethyl, propyl or longer branched alkyl chains, the branched oligo-α-olefin being obtainable by oligomerization of a) at least one branched α-olefin containing 5 to 18 carbon atoms,
b) at least one linear α-olefin containing 4 to 10 carbon atoms,
c) a mixture of a branched α-olefin containing 4 to 18 carbon atoms and a linear α-olefin containing 3 to 18 carbon atoms or
d) a mixture of various branched α-olefins containing 4 to 18 carbon atoms and linear α-olefins containing 3 to 18 carbon atoms in the presence of a catalyst selected from the group consisting of organic acids, cationic ion exchangers, silica gels, layer silicates, inorganic acids or Lewis-acid-based catalysts. The specific oligo-α-olefins are distinguished by particularly high spreading power, by an improved sensory impression of the final cosmetic formulation and by particularly good stability in antiperspirant/deodorant formulations.

3 Claims, No Drawings

COSMETIC OLIGO-α-OLEFIN CONTAINING COMPOUND

CROSS-REFERENCE TO RELATED APPLICATIONS

This application is filed under 35 U.S.C. §371 claiming priority from application PCT/EP2004/003693 filed on Apr. 7, 2004, which claims priority from German applications No. 103 17 781.7 filed on Apr. 16, 2003; No. 103 24 508.1 filed on May 28, 2003; and No. 103 36 172.3 filed on Aug. 7, 2003, the entire contents of each application are incorporated herein by reference.

BACKGROUND OF THE INVENTION

1. Technical Field

This invention relates to new cosmetic compositions containing certain branched oligo-α-olefins and to the use of these branched oligo-α-olefins as oil components in cosmetic and pharmaceutical preparations.

2. Background Art

Consumers expect cosmetic skin- and hair-care emulsions to satisfy a range of requirements. Apart from the cleaning and skin-/hair-care effects which determine the intended application, value is placed on such diverse parameters as very high dermatological compatibility, good lipid-layer-enhancing properties, elegant appearance, optimal sensory impression and stability in storage.

Besides a number of surfactants, preparations used to clean and care for the human skin and hair contain, above all, oil components and water. The oil components/emollients used include, for example, hydrocarbons, ester oils and vegetable and animal oils/fats/waxes. In order to meet stringent commercial requirements in regard to sensory properties and optimal dermatological compatibility, new oil components and emulsifier mixtures are continually being developed and tested. A large number of natural and synthetic oils, for example almond or avocado oil, ester oils, ethers, alkyl carbonates, hydrocarbons and silicone oils, are used in the production of cosmetic or pharmaceutical preparations. A key function of the oil components—besides their care effect which is directly related to lipid layer enhancement of the skin—is to provide the skin of consumers with a non-sticky, almost instantaneous and long-lasting feeling of smoothness and suppleness.

The subjective feeling on the skin can be correlated and objectivized with the physicochemical parameters of the spreading of the oil components on the skin, as illustrated by U. Zeidler in the journal *Fette, Seifen, Anstrichmittel* 87, 403 (1985). According to this reference, cosmetic oil components can be classified as low-spreading (<300 mm$^2$/10 mins.), medium-spreading (>/=300 to 1000 mm$^2$/10 mins.) and high-spreading oils (>/=1000 mm$^2$/10 mins.). If a high-spreading oil is used as the oil component in a predetermined formulation, the required feeling of smoothness of the skin is achieved very quickly and, where cyclomethicones, for example Dow Corning 245 fluid (Dow Corning Corporation) or Abil® B 8839 (Goldschmidt Chemical Corporation), are used, a velvety feeling desirable to the consumer is also obtained. Unfortunately, the experience does not last long because the high volatility of the last-mentioned structures means that the pronounced feeling of smoothness and hence the velvety feel disappear very quickly, leaving the skin with an unpleasant, dull feeling.

However, cyclomethicones have the advantage over other hydrocarbon-based emollients, such as very light mineral oils, polybutylenes (for example Arlamol® HD, ICI), ethyl hexyl cyclohexane (Cetiol®) S, Cognis Deutschland GmbH & Co. KG), that they have a very light feeling on the skin. Accordingly, there is a need for hydrocarbon-based oil components/emollients which combine the advantages of the cyclomethicones, such as a light feeling on the skin and good spreading properties, without having any of their disadvantages.

The use of tetraisobutylene in cosmetic compositions is known from EP 1 232 739 or EP 1 103 249.

The problem addressed by the present invention was to provide improved, high-spreading oil components and preparations containing them which would impart an almost instantaneous and relatively long-lasting feeling of smoothness to the skin and which would show good dermatological compatibility. In addition, the oil components would lend themselves to simple and stable incorporation in emulsions, would be hydrolysis-stable in the event of pH variations and would lead to low-viscosity compositions imparting a very light feeling on the skin. Another aspect of the stated problem was to provide oil components for antiperspirants/deodorants which would be comparatively unaffected by hydrolysis and would allow stable formulations in the presence of the astringent aluminium and zirconium compounds.

BRIEF SUMMARY OF THE INVENTION

The present invention relates to a cosmetic composition containing at least one branched oligo-α-olefin, characterized in that the side chains at one branch point at least are ethyl, propyl or longer branched alkyl chains, the branched oligo-α-olefin being obtainable by oligomerization of a) at least one branched α-olefin containing 5 to 18 carbon atoms, b) at least one linear α-olefin containing 4 to 10 carbon atoms, c) a mixture of a branched α-olefin containing 4 to 18 carbon atoms and a linear α-olefin containing 3 to 18 carbon atoms or d) a mixture of various branched α-olefins containing 4 to 18 carbon atoms and linear α-olefins containing 3 to 18 carbon atoms in the presence of a catalyst selected from the group consisting of organic acids, cationic ion exchangers, silica gels, layer silicates, inorganic acids or Lewis-acid-based catalysts.

The specific oligo-α-olefins are distinguished by particularly high spreading power, by an improved sensory impression of the final cosmetic formulation and by particularly good stability in antiperspirant/deodorant formulations.

DETAILED DESCRIPTION OF THE INVENTION

In the context of the present invention, oligo-α-olefins are understood to be dimers, trimers, tetramers, pentamers and hexamers of the α-olefins, the use of dimers, trimers, tetramers and pentamers being preferred. The conditions for the oligomerization and subsequent hydrogenation are well-known to the expert. The production of oligomers using BF$_3$-containing catalysts or metallocen catalysts is described, for example, in WO 98/20053, DE 27 026 04, U.S. Pat. No. 5,068,490, U.S. Pat. No. 5,286,823 or WO 85/01942. The reaction conditions are selected according to the required degree of oligomerization and the required iodine value and are monitored and adjusted during the reaction by the usual analysis methods known to the expert.

The branched specific oligo-α-olefins used in the cosmetic composition according to the invention are odorless, colorless or yellowish products which may be liquid or solid according to chain length. There is no exact structural formula for the oligo-α-olefins because, basically, the oligomerization reaction gives product mixtures of which the fractions can be separated, for example, by distillation.

Suitable organic acid catalysts are, for example, p-toluenesulfonic acid, alkyl benzenesulfonic acid, methanesulfonic acid or $C_{2-4}$ mono-, di- or tricarboxylic acids, such as sulfosuccinic acid for example. Lewatit® SPC 112 (Bayer AG) is a suitable cationic ion exchanger. The Lewis-acid-based catalysts include, for example, boron halides, aluminium halides and aluminium alkyl halides.

Preferred cosmetic compositions are those in which the branched oligo-α-olefin contains 12 to 36, preferably 12 to 24 and more particularly 14 to 24 carbon atoms. Cosmetic compositions based on branched oligo-α-olefins containing 16 to 20 carbon atoms are most particularly preferred. In another preferred embodiment of the invention, the branched oligo-α-olefins resulting from the oligomerization are subsequently hydrogenated. The hydrogenation may be carried out on the technical product mixture directly resulting from the oligomerization. However, it may also be carried out after separation of the fractions by distillation. The additional hydrogenation step leads to products with greater resistance to oxidation. Possible hydrogenation conditions are described, for example, in International application PCT/EP02/11392. Suitable catalysts are the hydrogenation catalysts known from the prior art, such as nickel or the noble metal catalysts, more particularly based on platinum or palladium. Particularly suitable noble metal catalysts are palladium catalysts, more particularly palladium on coal.

Among the products obtained by oligomerization of the linear α-olefins b) containing 4 to 10 carbon atoms, tetramers are preferred. Tetramers of 1-butene and 2-butene are particularly suitable. According to the invention, it is also preferred to use the oligo-α-olefins which are typically formed as secondary products during the polymerization of 1-butene or mixtures of 1-butene and 2-butene in the production of isotridecyl alcohols and which can be isolated from the bottom product. An industrially practised process is, for example, the Octol process of UOP and Degussa-Hüls AG in which $C_3$ and $C_4$ olefins are reacted on a catalyst, for example on phosphoric acid applied to $SiO_2$, at 30° C. to 250° C./20 to 80 bar pressure to form higher olefins with a high degree of branching. This process is described inter alia in Petrochemical Processes, Vol. 1, Editions Technip (1989), pp. 183-187 and in Hydrocarbon Processing, February 1992, pp. 45-46.

In another preferred embodiment, the cosmetic composition contains branched oligo-α-olefins obtained by oligomerizing a mixture of a branched α-olefin containing 5 to 12 carbon atoms and a linear α-olefin containing 3 to 12 carbon atoms in the presence of a catalyst selected from the group of organic acids, cationic ion exchangers, silica gels, layer silicates, inorganic acids or Lewis-acid-based catalysts and then optionally hydrogenating the oligomerization product.

Preferred linear α-olefins are selected from the group consisting of 1-propene, 1-butene, 2-butene, 1-pentene and 2-pentene. Preferred branched α-olefins are selected from the group consisting of 2-ethyl-1-hexene, 2-propyl heptene, 2-methyl-1-butene, 2-methyl-1-pentene, 3-methyl-1-pentene and 4-methyl-1-pentene.

Another preferred embodiment of the cosmetic composition contains branched oligo-α-olefins which are obtainable by oligomerizing a mixture of 80% butene and 20% isobutene in the presence of a catalyst selected from the group of organic acids, cationic ion exchangers, silica gels, layer silicates, inorganic acids or Lewis-acid-based catalysts and then optionally hydrogenating the oligomerization product.

The specific branched oligo-α-olefins are eminently suitable for use as oil components in cosmetic or pharmaceutical preparations. Accordingly, the present invention also relates to the use of at least one oligo-α-olefin obtainable by oligomerization of a) at least one branched α-olefin containing 5 to 18 carbon atoms, b) at least one linear α-olefin containing 4 to 10 carbon atoms, c) a mixture of a branched α-olefin containing 4 to 18 carbon atoms and a linear α-olefin containing 3 to 18 carbon atoms or d) a mixture of various branched α-olefins containing 4 to 18 carbon atoms and linear α-olefins containing 3 to 18 carbon atoms in the presence of a catalyst selected from the group consisting of organic acids, cationic ion exchangers, silica gels, layer silicates, inorganic acids or Lewis-acid-based catalysts and subsequent hydrogenation of the oligomerization product, as oil components in cosmetic or pharmaceutical preparations, more particularly in antiperspirant and/or deodorant formulations. The use of these oligo-α-olefins in antiperspirant formulations based on astringent aluminium and, in particular, aluminium/zirconium complexes leads to particularly storage-stable and hydrolysis-resistant compositions.

Cosmetic Preparations

The compound according to the invention allows the production of stable cosmetic emulsions. These cosmetic emulsions are preferably body care formulations, for example in the form of creams, milks, lotions, sprayable emulsions, products for eliminating body odor, etc. The compound according to the invention may also be used in surfactant-containing formulations such as, for example, foam and shower baths, hair shampoos and care rinses.

The cosmetic preparations may be formulated as emulsions or dispersions which contain water and the oil phase alongside one another. Preferred cosmetic compositions are those in the form of a w/o or o/w emulsion with the usual concentrations—known to the expert—of oils/fats/waxes, emulsifiers, water and the other auxiliaries and additives typically used in cosmetic preparations.

The cosmetic composition according to the invention contains 1 to 50% by weight, preferably 5 to 40% by weight and more particularly 5 to 25% by weight oil of components which, together for example with oil-soluble surfactants/emulsifiers and oil-soluble active components, form part of the so-called oil or fatty phase. In the context of the invention, the oil components include fatty compounds, waxes and liquid oils, but not emulsifiers/surfactants. The poly-α-olefins may be present as sole oil component or in combination with other oils/fats/waxes. The percentage content of the at least one oligo-α-olefin, based on the total quantity of oil components, is 0.1 to 100% by weight and preferably 1 to 50% by weight. Quantities of 1 to 20% by weight are particularly preferred.

Depending on the particular application envisaged, the cosmetic formulations contain a number of other auxiliaries and additives, such as, for example, surface-active substances (surfactants, emulsifiers), other oil components, pearlizing waxes, consistency factors, thickeners, superfatting agents, stabilizers, polymers, silicone compounds, fats, waxes, lecithins, phospholipids, biogenic agents, UV protection factors, antioxidants, deodorants, antiperspirants, antidandruff agents, film formers, swelling agents, insect repellents, self-tanning agents, tyrosinase inhibitors (depigmenting agents), hydrotropes, solubilizers, preservatives, perfume oils, dyes, etc. which are listed by way of example in the following.

The quantities of the particular additives are governed by the particular application envisaged.

Surface-Active Substances

In another preferred embodiment, the cosmetic composition contains 0.1 to 20% by weight, preferably 1 to 15% by weight and more particularly 1 to 10% by weight of a surface-active substance or a mixture of surface-active substances.

The surface-active substances present may be anionic, nonionic, cationic and/or amphoteric or zwitterionic surfactants or emulsifiers or a mixture thereof. In surfactant-containing cosmetic preparations such as, for example, shower gels, foam baths, shampoos, etc., at least one anionic surfactant is preferably present. Body-care creams and lotions preferably contain nonionic surfactants/emulsifiers.

Typical examples of anionic surfactants are soaps, alkyl benzene-sulfonates, alkanesulfonates, olefin sulfonates, alkylether sulfonates, glycerol ether sulfates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, polyglycerol esters, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, amino-propionates, aminoglycinates, imidazolinium betaines and sulfobetaines. The surfactants mentioned are all known compounds. Information on their structure and production can be found in relevant synoptic works in this field. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligo-glucosides, fatty acid glucamides, alkylamidobetaines, amphoacetals and/or protein fatty acid condensates, preferably based on wheat proteins.

Oil Components

Body care preparations, such as creams, lotions and milks, normally contain a number of other oil components and emollients which contribute towards further optimizing their sensory properties. Suitable oil components are, for example, Guerbet alcohols based on fatty alcohols containing 6 to 18 and preferably 8 to 10 carbon atoms, esters of linear $C_{6-22}$ fatty acids with linear or branched $C_{6-22}$ fatty alcohols or esters of branched $C_{6-13}$ carboxylic acids with linear or branched $C_{6-22}$ fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_{6-22}$ fatty acids with branched alcohols, more particularly 2-ethyl hexanol and isopropanol, esters of $C_{18-38}$ alkylhydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, such as Dicaprylyl Carbonate (Cetiol® CC) for example, Guerbet carbonates based on $C_{6-18}$ and preferably $C_{8-10}$ fatty alcohols, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, such as Dicaprylyl Ether (Cetiol® OE) for example, ring opening products of epoxidized fatty acid esters with polyols, silicone oils (cyclomethicone, silicon methicone types, etc.) and/or aliphatic or naphthenic hydrocarbons such as, for example, mineral oil, Vaseline, petrolatum, isohexadecanes, squalane, squalene or dialkyl cyclohexanes.

Fats and Waxes

Fats and waxes are added to the body care products both as care components and to increase the consistency of the cosmetic preparations. Typical examples of fats are glycerides, i.e. solid or liquid, vegetable or animal products which consist essentially of mixed glycerol esters of higher fatty acids. Fatty acid partial glycerides, i.e. technical mono- and/or di-esters of glycerol with $C_{12-18}$ fatty acids, such as for example glycerol mono/dilaurate, palmitate or stearate, may also be used for this purpose. Suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Thickeners

Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, polyacrylates (for example Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone. Other consistency factors which have proved to be particularly effective are bentonites, for example Bentone® Gel VS-5PC (Rheox) which is a mixture of cyclopentasiloxane, Disteardimonium Hectorite and propylene carbonate, and a sodium polyacrylate known as Cosmedia® SP. Other suitable consistency factors are electrolytes, such as sodium chloride and ammonium chloride.

Stabilizers

Metal salts of fatty acids such as, for example, magnesium, aluminium and/or zinc stearate or ricinoleate may be used as stabilizers.

UV Protection Factors and Antioxidants

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzo-phenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone or Dioctyl Butamido Triazone (Uvasorb® HEB);

propane-1,3-diones such as, for example, 1-(4-tert.butylphenyl)-3-(4'-methoxyphenyl)-propane-1,3-dione;

ketotricyclo(5.2.1.0)decane derivatives.

Suitable water-soluble substances are 2-phenylbenzimidazole-5-sulfonic acid and alkali metal, alkaline earth metal, ammonium, alkylammonium, alkanolammonium and glucammonium salts thereof and 2,2'-(1, 4-phenylene)-bis-1H-benzimidazole-4,6-disulfonic acid and salts thereof, more particularly the sodium salt;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol® 1789) or 1-phenyl-3-(4'-isopropylphenyl)-propane-1,3-dione and enamine compounds. The UV-A and UV-B filters may of course also be used in the form of mixtures. Particularly favorable combinations consist of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide. Silicates (talcum), barium sulfate and zinc stearate may be used as salts. The oxides and salts are used in the form of the pigments for skin-care and skin-protecting emulsions.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin.

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes.

Deodorants

Deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Germ Inhibitors

Basically, suitable germ inhibitors are any substances which act against gram-positive bacteria such as, for example, 4-hydroxybenzoic acid and salts and esters thereof, N-(4-chlorophenyl)-N'-(3,4-dichlorophenyl)-urea, 2,4,4'- trichloro-2'-hydroxydiphenylether (triclosan), 4-chloro-3,5-dimethylphenol, 2,2'-methylene-bis-(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), salicylic acid-N-alkylamides such as, for example, salicylic acid-n-octyl amide or salicylic acid-n-decyl amide.

Enzyme Inhibitors

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Odor Absorbers

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants.

Antiperspirants

Antiperspirants reduce perspiration and thus counteract underarm wetness and body odor by influencing the activity of the eccrine sweat glands. By virtue of their hydrolysis stability and compatibility with antiperspirant active principles, the specific oligo-α-olefins mentioned in claim 1 are particularly suitable for the antiperspirant sector. Accordingly, another preferred embodiment are cosmetic compositions, characterized in that they additionally contain at least one antiperspirant and/or deodorant active principle, preferably an aluminium-zirconium salt.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example with amino acids, such as glycine.

Antidandruff Agents

Suitable antidandruff agents are piroctone olamine (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Insect Repellents

Suitable insect repellents are N,N-diethyl-m-toluamide, pentane-1,2-diol or 3-(N-n-butyl-N-acetylamino)-propionic acid ethyl ester), which is marketed under the name of Insect Repellent® 3535 by Merck KGaA, and butyl acetylaminopropionate.

Self-Tanning Agents and Depigmenting Agents

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Hydrotropes

In addition, hydrotropes, for example ethanol, isopropyl alcohol or polyols, may be used to improve flow behavior. Suitable polyols preferably contain 2 to 15 carbon atoms and at least two hydroxyl groups.

Preservatives

Suitable preservatives are, for example, phenoxyethanol, formal-dehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Perfume Oils and Aromas

Suitable perfume oils are mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, and synthetic perfume compounds of the ester, ether, aldehyde, ketone, alcohol and hydrocarbon type may also be used.

Dyes

Suitable dyes are any of the substances suitable and approved for cosmetic purposes. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). These dyes are normally used in concentrations of 0.001 to 0.1% by weight, based on the mixture as a whole.

EXAMPLES

Example 1

560 g 2-ethyl-1-hexene is oligomerized with Lewatit® SPC 112 (Bayer AG) for 3 hours at 100° C./10 bar pressure.

380 g of the resulting oligo-α-olefin are hydrogenated with 100 bar hydrogen for 12 hours at 200° C. in the presence of 0.05% palladium on coal.

Example 2

700 g 2-propyl-1-heptene is oligomerized with Lewatit® SPC 112 (Bayer AG) for 3 hours at 100° C./10 bar pressure. 380 g of the resulting oligo-α-olefin are hydrogenated with 100 bar hydrogen for 12 hours at 200° C. in the presence of 0.05% palladium on coal.

Example 3

500 g of an olefin mixture (90% by weight isobutene and 10% by weight 1-pentene) is oligomerized with Lewatit® SPC 112 (Bayer AG) for 3 hours at 100° C./10 bar pressure. 380 g of the oligomerized α-olefin are hydrogenated with 100 bar hydrogen for 12 hours at 200° C. in the presence of 0.05% palladium on coal.

Example 4

500 g of an olefin mixture (80% by weight isobutene and 20% by weight 1-pentene) is oligomerized with Lewatit® SPC 112 (Bayer AG) for 3 hours at 100° C./10 bar pressure. 380 g of the oligomerized α-olefin are hydrogenated with 100 bar hydrogen for 12 hours at 200° C. in the presence of 0.05% palladium on coal.

Example 5

500 g of an olefin mixture (80% by weight isobutene and 20% by weight 1-butene) is oligomerized with Lewatit® SPC 112 (Bayer AG) for 3 hours at 100° C./10 bar pressure. 380 g of the oligomerized α-olefin are hydrogenated with 100 bar hydrogen for 12 hours at 200° C. in the presence of 0.05% palladium on coal.

Example 6

An oligo-1-but-1-ene is obtained from 1-butene in accordance with WO 98/20053. The tetramer is obtained from the oligomer mixture by fractionation.

To this end, triisobutyl aluminoxane is prepared in accordance with EP-A-575 356. 35 g of a solution of isobutyl aluminoxane in heptane (3% by weight, based on Al; 38.9 mmol Al), 2.7 g trimethyl aluminium and 180 g 1-butene are successively introduced into a reaction vessel under an inert gas, followed by the addition of solid bis-cyclopentadienyl zirconium(IV) chloride (3.2 g). After heating for ca. 22 h to 50° C., 10% hydrochloric acid is added while cooling with ice. The organic phase is removed, the solvent is distilled off and the oligomer mixture is separated by fractionation into trimers, tetramers, pentamers and hexamers. The tetramer was hydrogenated as described in Examples 1-5.

Example 7

An oligo-1-pentene is obtained from 1-pentene by the method described in Example 6. The trimer is obtained from the oligomer mixture by fractionation.

To this end, triisobutyl aluminoxane is prepared in accordance with EP-A-575 356. 35 g of a solution of isobutyl aluminoxane in heptane (3% by weight, based on Al; 38.9 mmol Al), 2.7 g trimethyl aluminium and 200 g 1-pentene are successively introduced into a reaction vessel under an inert gas, followed by the addition of solid bis-cyclopentadienyl zirconium(IV) chloride (3.2 g). After heating for ca. 22 h to 50° C., 10% hydrochloric acid is added while cooling with ice. The organic phase is removed, the solvent is distilled off and the oligomer mixture is fractionated. The trimer was hydrogenated as described in Examples 1-5.

Example 8

560 g 2-ethyl-1-hexene is oligomerized with Lewatit® SPC 112 (Bayer AG) for 3 hours at 100° C./10 bar pressure. 380 g of the resulting mixture are hydrogenated with 100 bar hydrogen for 12 hours at 200° C. in the presence of 0.05% palladium on coal. The mixture obtained after hydrogenation consists of 75% by weight dimer (=isohexadecane=C16), 20% by weight trimer (=isotetracosane=C24) and 5% by weight tetramer (=iso-C32-hydrocarbon).

Cosmetic Compositions

The following emulsions can be prepared using the oligo-α-olefins of Example 1 as oil component:

Example 8 o/w Emulsion

| | |
|---|---|
| Eumulgin ® B2 | 2% by weight |
| Lanette ® O | 5% by weight |
| Oligo-α-olefin | 16% by weight |
| Glycerol | 3% by weight |
| Water | 73.85% by weight |
| Formalin (37%) | 0.15% by weight |

Example 9 o/w Emulsion

| | |
|---|---|
| Eumulgin ® VL 75 | 4.5% by weight |
| Oligo-α-olefin | 16% by weight |
| Carbopol ® | 0.3% by weight |
| KOH (20%) | 0.7% by weight |
| Glycerol | 3% by weight |
| Water | 75.35% by weight |
| Formalin (37%) | 0.15% by weight |

Example 10 w/o Emulsion

| | |
|---|---|
| Dehymuls ® PGPH | 5% by weight |
| Oligo-α-olefin | 20% by weight |
| Glycerol | 5% by weight |
| Mg sulfate•7H$_2$O | 1% by weight |
| Water | 68.85% by weight |
| Formalin (37%) | 0.15% by weight |

Examples of formulations which demonstrate the various potential applications of the cosmetic compositions according to the invention are presented in the following. All quantities represent percentages by weight of the commercially available substances in the composition as a whole.

TABLE 1

O/W sun protection emulsions

| Component | 1 | 2 | 3 | 4 | 5 | 6 | 7 | 8 | 9 | 10 | 11 |
|---|---|---|---|---|---|---|---|---|---|---|---|
| L = Lotion, C = Cream | L | C | S | L | C | L | L | C | L | C | L |
| Eumulgin ® VL 75 | | | | | | 4 | 4 | 2 | | | |
| Eumulgin ® B2 | 2 | | | | | | | | | | |
| Tween ® 60 | | | | 1 | | | | | | | |
| Myrj ® 51 | | 3 | | 2 | | | | | | | |
| Cutina ® E 24 | 1 | | | 1 | | | | | | | |
| Hostaphat ® KL 340 N | | | | | | | | | 2 | | |
| Lanette ® E | | | 0.5 | | | | | 0.5 | | | |
| Amphisol ® K | | | 1 | | | 1 | | 0.5 | | 1 | |
| Sodium stearate | | | | | | | | 1 | | | 2 |
| Emulgade ® PL 68/50 | | | 1 | | 5 | | | | 4 | | |
| Tego ® Care 450 | | | | | | | | | 3 | | |
| Cutina ® MD | 2 | | | 6 | | | 4 | | | 6 | |
| Lanette ® 14 | 1 | | | 1 | | | | 2 | | | 4 |
| Lanette ® O | 1 | 6 | | | 5 | 2 | | 2 | | | |
| Antaron V 216 | | | 1 | | 2 | 2 | | | | 1 | |
| Emery ® 1780 | | | | | 0.5 | 0.5 | | | | | |
| Lanolin, anhydrous, USP | | | | | | | 5 | | | | |
| Oligo-α-olefin (Example 1) | 2 | 2 | 4 | 1 | 2 | 2 | 2 | 1 | 2 | 2 | 1 |
| Myritol ® PC | | | | | 5 | | | | | | |
| Myritol ® 331 | 5 | | 8 | | | 6 | | 10 | | 2 | |
| Finsolv ® TN | | | 1 | | | | | 1 | 8 | | |
| Cetiol ® CC | | 2 | 5 | | | 4 | 4 | 2 | | 2 | |
| Cetiol ® OE | | | 3 | | | | | | 2 | 3 | |
| Dow Corning DC ® 345 | 4 | | 1 | | 5 | | | 2 | | 2 | |
| Dow Corning DC ® 2502 | | 1 | | | 2 | | | | | | |
| Squatol ® S | | | | | | | 4 | | | | |
| Silikonöl Wacker AK ® 350 | | 2 | | | | | | | | | |
| Cetiol ® 868 | | | | | 2 | | 4 | | | | 7 |
| Cetiol ® J 600 | | | | | 3 | 2 | | | | 5 | |
| Mineral oil | | | | 9 | | | | | | | |
| Cetiol ® B | | | 1 | | | | | | | 2 | |
| Eutanol ® G | | | | | | | | | | | |
| Eutanol ® G 16 | | | | | | | | | | | |
| Cetiol ® PGL | | | 5 | | | | | | | 5 | |
| Almond oil | | | 2 | | | | | 1 | | | |
| Photonyl ® LS | | | | 2 | | | | | | 2 | |
| Panthenol | | | | | | 1 | | | | | |
| Bisabolol | | | | | | | | 0.2 | | | |
| Tocopherol/Tocopherylacetate | | | | | | | | 1 | | | |
| Photonyl ® LS | | | | | | | | | | | |
| Neo Heliopan ® Hydro (Na salt) | 2 | | 2.2 | | 3 | 3 | | | | 2 | |
| Neo Heliopan AP (Na salt) | 2 | | | | 1.5 | 2 | 2 | | 1 | | 1 |
| Neo Heliopan ® 303 | 3 | 5 | 9 | 4 | | | | | | | 2 |
| Neo Heliopan ® BB | | | | | 1 | | | | | | |
| Neo Heliopan ® MBC | 2 | | | 3 | | 2 | 2 | 2 | | | 1 |
| Neo Heliopan ® OS | | | | | | | | | 10 | 7 | |
| Neo Heliopan ® E 1000 | | 7.5 | | 6 | | | | | | | 6 |
| Neo Heliopan ® AV | | | 7.5 | | | 7.5 | 4 | 5 | | | |
| Uvinul ® T 150 | 2 | | | | 2.5 | | | 1 | | | |
| Parsol ® 1789 | | 1 | 1 | | | | 2 | | 2 | 2 | |
| Zinc oxide NDM | 10 | | 5 | | | 10 | | 3 | | 5 | 4 |
| Eusolex ® T 2000 | | | | | 5 | | 3 | 3 | | | 4 |
| Veegum ® Ultra | | | 0.7 | | | | | 1 | 1 | | |
| Keltrol ® T | | | 0.2 | | | | | 0.5 | 0.5 | | |
| Carbopol ® 980 | | 0.5 | | 0.2 | 0.2 | 0.2 | | 0.5 | 0.1 | 0.3 | 0.2 |
| Ethanol | | | | | | | | | 10 | | |
| Butylene glycol | | 2 | | 4 | 3 | | 2 | 5 | 2 | | 2 |
| Glycerin | 5 | 5 | 5 | | 3 | 3 | | | 4 | | 3 |
| Preservative, NaOH | | | | | | q.s. | | | | | |
| Water | | | | | | to 100 | | | | | |

TABLE 2

O/W sun protection emulsions

| Component | 12 | 13 | 14 | 15 | 16 | 17 | 18 | 19 | 20 | 21 | 22 |
|---|---|---|---|---|---|---|---|---|---|---|---|
| L = Lotion, C = Cream | L | L | L | C | L | C | S | C | C | L | L |
| Eumulgin ® VL 75 | 4 | 3 | 4.5 | | 3 | | | | 4 | | |
| Eumulgin ® B2 | | | | | | | | | | 1 | |

TABLE 2-continued

O/W sun protection emulsions

| Component | 12 | 13 | 14 | 15 | 16 | 17 | 18 | 19 | 20 | 21 | 22 |
|---|---|---|---|---|---|---|---|---|---|---|---|
| Tween ® 60 | | | | | | | | | | 1 | |
| Myrj ® 51 | | | | | | | | | | | |
| Cutina ® E 24 | | | | 2 | | | | | | | |
| Hostaphat ® KL 340 N | | | | | | | | | | 0.5 | |
| Lanette ® E | 0.5 | | 0.5 | 0.5 | | | 0.1 | | 0.5 | | |
| Amphisol ® K | 0.5 | | | | | 1 | 1 | 1 | | | |
| Sodium stearate | | | | | 1 | | | | | | |
| Emulgade ® PL 68/50 | | 6 | | | | 4.5 | 1 | 5 | | | |
| Tego ® Care 450 | 1 | | | | | | | | 4 | | |
| Cutina ® MD | 1 | | | 8 | 6 | 1 | | | | 4 | 1 |
| Lanette ® 14 | | 2 | | | | | | 2 | | 1 | |
| Lanette ® O | | | 2 | | | | | | 1 | 1 | |
| Antaron V 220 | 1 | | | 2 | | | 0.5 | | | 2 | 0.5 |
| Oligo-α-olefin (Example 1) | 4 | 2 | 4 | 6 | 10 | 4 | 2 | 8 | 2 | 1 | 3 |
| Myritol ® PC | | | | | | | | | 5 | | |
| Myritol ® 331 | 12 | | 12 | | | 8 | 8 | | | 10 | 8 |
| Finsolv ® TN | | | | | 5 | | | 3 | 3 | | |
| Cetiol ® CC | 6 | | 6 | | | 5 | 5 | | | | |
| Cetiol ® OE | | | | | 2 | | | | | | 2 |
| Dow Corning DC ® 345 | | 2 | | | 1 | | | | | | |
| Dow Corning DC ® 2502 | | 1 | | | 1 | | | | | | |
| Ceraphyl ® 45 | | | | | | | | | | 2 | 2 |
| Silikonöl Wacker AK ® 350 | | | | | 1 | | | | | | |
| Cetiol ® 868 | | 2 | | | | | | | | | |
| Cetiol ® J 600 | | 2 | | | | | | | | | |
| Mineral oil | | | | 10 | | | | | | | |
| Cetiol ® B | 4 | | 4 | | | | | 4 | | | |
| Eutanol ® G | | 3 | | | | 3 | | | | | |
| Eutanol ® G 16 S | 10 | | | | | | | | | | |
| Cetiol ® PGL | | | | | | | | | 2 | | |
| Photonyl ® LS | | | | | | | | | | 2 | |
| Panthenol | | | | | | 1 | | | | | |
| Bisabolol | | | | | | 0.2 | | | | | |
| Tocopherol/Tocopherylacetate | | | | | | 1 | | | | | |
| Neo Heliopan ® Hydro (Na salt) | | | | | | | | | | 3 | |
| Neo Heliopan AP (Na salt) | | 2 | | 2 | | | 2 | | | | 1 |
| Eusolex ® OCR | 6 | | 9 | | 5 | 7 | 9 | | 4 | | 7 |
| Neo Heliopan ® BB | | | | | | | | 1 | 1 | | 1 |
| Neo Heliopan ® MBC | | 2 | | 1 | | | | 3 | 1 | | 3 |
| Neo Heliopan ® OS | 2 | | | | | | | | 7 | | |
| Neo Heliopan ® E1000 | | 4 | | | | | | 5 | | | |
| Neo Heliopan ® AV | | 4 | 7.5 | 5 | | | | 5 | 4 | 7.5 | |
| Uvinul ® T 150 | 1 | | | | | | | | 1.3 | 1 | 1 |
| Parsol ® 1789 | 1 | | | | | | | | 2 | | 1 |
| Z-Cote ® HP 1 | 7 | 2 | 5 | | | 7 | 5 | | 6 | 2 | |
| Eusolex ® T 2000 | 5 | 2 | | | 10 | | 10 | | | 2 | |
| Veegum ® Ultra | 1.5 | | 1.5 | | | 1.5 | 1.2 | | 1 | | |
| Keltrol ® T | 0.5 | | 0.5 | | | 0.5 | 0.4 | | 0.5 | | |
| Pemulen ® TR 2 | | 0.3 | | 0.3 | | | 0.1 | 0.2 | | | 0.3 |
| Ethanol | | 5 | | 8 | | | | | | | |
| Butylene glycol | 1 | | | 3 | 3 | | | | | 8 | 1 |
| Glycerin | 2 | 4 | 3 | 3 | | 3 | 3 | 3 | 5 | | 3 |
| Water/preservative/NaOH | | | | | to 100/q.s./q.s | | | | | | |

TABLE 3

W/O sun protection emulsions

| Component | 23 | 24 | 25 | 26 | 27 | 28 | 29 | 30 | 31 | 32 | 33 |
|---|---|---|---|---|---|---|---|---|---|---|---|
| L = Lotion; C = Cream | C | L | C | L | C | L | L | L | L | C | C |
| Dehymuls ® PGPH | 4 | 2 | 1 | 3 | 3 | 1 | 1 | 2 | 2 | 4 | 1 |
| Monomuls ® 90-O18 | | | 2 | | | | | | | | |
| Lameform ® TGI | 2 | | 4 | | 3 | | | | | 1 | 3 |
| Abil ® EM 90 | | | | | | | 4 | | | | |
| Glucate ® DO | | | | | | | | | | | 3 |
| Isolan ® PDI | | | | | | 4 | | 2 | | | |
| Arlacel ® 83 | | | | 2 | | | | | | | |
| Elfacos ® ST9 | | | | | | | | | 2 | | |
| Elfacos ® ST37 | | | | | | | | | | | |

TABLE 3-continued

W/O sun protection emulsions

| Component | 23 | 24 | 25 | 26 | 27 | 28 | 29 | 30 | 31 | 32 | 33 |
|---|---|---|---|---|---|---|---|---|---|---|---|
| Arlacel ® P 135 | | 2 | | | | | | | | | |
| Dehymuls ® HRE 7 | | | | | | | | | | | |
| Zinc stearate | 1 | | | 1 | 1 | | | 1 | | 1 | |
| Microcrystalline wax | | | 5 | | | 2 | | | 5 | | 5 |
| Beeswax | 1 | | | 1 | | | | 5 | | 7 | |
| Tego ® Care CG | | | | | 1 | | | | | | .5 |
| Prisorine ® 3505 | 1 | | 1 | 1 | | 1 | 1 | | | | 1 |
| Emery ® 1780 | | | 5 | | | | | | | 4 | |
| Wool wax alcohol, anhydrous, USP | | | | | | | | | | | 1 |
| Antaron V 216 | 2 | | | | | | | | | | |
| Oligo-α-olefin (Example 1) | 3 | 4 | 2 | 1 | 10 | 2 | 2 | 6 | 3 | 12 | 1 |
| Myritol ® PC | | | | | 3 | | | 4 | | | |
| Myritol ® 331 | 10 | | | | 3 | 6 | | | | | 8 |
| Finsolv ® TN | | | 5 | | | | 5 | | | | |
| Cetiol ® CC | 12 | 22 | | | | 2 | | 2 | | | 5 |
| Cetiol ® OE | | | | | 4 | | 5 | 4 | 2 | | |
| Dow Corning DC ® 345 | | | | | | | 2 | | | | |
| Dow Corning DC ® 2502 | | | 1 | | 2 | | | | | | |
| Prisorine ® 3758 | | | | | | | | | | 2 | |
| Silikonöl Wacker AK ® 350 | | | | 4 | | | | 3 | | | |
| Cetiol ® 868 | | | | | | | | | | 2 | |
| Eutanol ® G 16 | | 3 | | | | | | | | | |
| Eutanol ® G 16S | | | | | | | | | | | |
| Cetiol ® J 600 | | | 4 | | | 2 | | | | | |
| Ceraphyl ® 45 | | | | 2 | | | | 2 | | 6 | |
| Mineral oil | | | | | 4 | | | | | | |
| Cetiol ® B | | | 2 | 4 | | | | | | 3 | |
| Eutanol ® G | | | 3 | | | | | 8 | | | |
| Cetiol ® PGL | | 11 | | | | 4 | | | 9 | | |
| Almond oil | | | | | 1 | | 5 | | | | |
| Photonyl ® LS | | 2 | | 1 | | | | | 4 | | |
| Panthenol | | | | | | 1.0 | | | | | |
| Bisabolol | | | | | | 0.2 | | | | | |
| Tocopherol/Tocopherylacetate | | | | | | 1.0 | | | | | |
| Magnesium sulfate × 7 water | 1 | | | | | | | | | | |
| Neo Heliopan ® Hydro (Na salt) | | 2 | | 3 | | | | 2 | | | |
| Neo Heliopan AP (Na salt) | 2 | 1 | | | 2 | | | 1 | 2 | | 1 |
| Neo Heliopan ® 303 | | | | | 4 | | | | | 6 | |
| Neo Heliopan ® BB | | 4 | 2 | | | | 2 | | | | |
| Neo Heliopan ® MBC | | | | | | | | 4 | | 3 | |
| Neo Heliopan ® OS | | | | | | | | | | | |
| Neo Heliopan ® E 1000 | | | | | | | | 5 | | | |
| Neo Heliopan ® AV | | 3 | 6 | 6 | | 7.5 | 7.5 | 5 | | | 7.5 |
| Uvinul ® T 150 | | | | | 2.5 | | | 1 | | 2 | |
| Parsol ® 1789 | | 2 | | | | | | 1 | | 2 | |
| Zinc oxide NDM | | | | | | 6 | | | | | |
| Eusolex ® T 2000 | 15 | | 10 | | 5 | | 4 | | | | 4 |
| Ethanol | | | | | | | | | 8 | | |
| Butylene glycol | | | 2 | 6 | | | 2 | 5 | | | 2 |
| Glycerin | 5 | 3 | 3 | | 5 | 3 | 2 | | 10 | 4 | |
| Water, preservative | to 100, q.s. | | | | | | | | | | |

TABLE 4

W/O sun protection emulsions

| Component | 34 | 35 | 36 | 37 | 38 | 39 | 40 | 41 | 42 | 43 | 44 |
|---|---|---|---|---|---|---|---|---|---|---|---|
| L = Lotion; C = Cream | L | C | L | L | C | L | L | L | L | C | C |
| Dehymuls ® PGPH | 3 | 1 | 5 | 1 | 1 | 3 | 2 | 4 | 0.5 | 1 | 4 |
| Monomuls ® 90-O18 | | 1 | | | | | | | | | |
| Lameform ® TGI | | | | | 4 | | | 1 | | 3 | 1 |
| Abil ® EM 90 | | | | 1 | | | | | | 2 | |
| Glucate ® DO | | | 3 | | | | | | 2 | | |
| Isolan ® PDI | | 3 | | | | | 4 | | | | |
| Arlacel ® 83 | | | | | | 3 | | | | | |
| Elfacos ® ST9 | | | | | | | | | | | 2 |
| Elfacos ® ST37 | 2 | | | | | | | | | | |
| Arlacel ® P 135 | | | | | | 3 | | | | | |
| Dehymuls ® HRE 7 | | | | | | | | | 4 | | |
| Zinc stearate | | | 2 | 2 | 1 | 1 | | | 1 | 1 | |
| Microcrystalline wax | | | | | 4 | | 1 | | | 4 | |

TABLE 4-continued

W/O sun protection emulsions

| Component | 34 | 35 | 36 | 37 | 38 | 39 | 40 | 41 | 42 | 43 | 44 |
|---|---|---|---|---|---|---|---|---|---|---|---|
| Beeswax | | 4 | | 2 | | | 1 | | 2 | | 1 |
| Tego ® Care CG | | | | | | | | | | | |
| Isostearic acid | 1 | 1 | | | | | 1 | 1 | | 1 | 1 |
| Emery ® 1780 | | 7 | 3 | | | | | | | | |
| Wool wax alcohol, anhydrous, USP | | | | | | | | | | | |
| Antaron V 220 | | 0.5 | 2 | 1 | 1 | 1 | | | | | |
| Oligo-α-olefin (Example 1) | 2 | 4 | 3 | 3 | 2 | 2 | 1 | 3 | 3 | 1 | 4 |
| Myritol ® PC | | | | | | | | | | | |
| Myritol ® 331 | 4 | 2 | 3 | | 5 | | | 8 | 5 | 4 | |
| Finsolv ® TN | | 5 | 5 | | | 7 | | | | | |
| Cetiol ® CC | 3 | 1 | | | | | 3 | 16 | | | 12 |
| Cetiol ® OE | | 3 | | 2 | | | 3 | | | | |
| Dow Corning DC ® 345 | | 4 | | 2 | | | | | | | |
| Dow Corning DC ® 2502 | | | | 1 | | | | | | | |
| Prisorine ® 3578 | | 1 | | | | | | | | | |
| Silikonöl Wacker AK ® 350 | | | | 1 | | | | | | | |
| Cetiol ® 868 | | | | | | | | | | | |
| Eutanol ® G 16 | | | | | | | | | | | 3 |
| Eutanol ® G 16S | | | | | | | | | | | 7 |
| Cetiol ® J 600 | | | | 3 | | | | | | | |
| Ceraphyl ® 45 | | | | 1 | | | | | 5 | 4 | |
| Mineral oil | | | | | | | 9 | | | | |
| Cetiol ® B | | | | | 3 | 3 | | 2 | 2 | | |
| Eutanol ® G | | | | 2 | | | | | 5 | | |
| Cetiol ® PGL | | | | | | | | 2 | | | |
| Almond oil | | | 2 | | | | | | | | |
| Photonyl ® LS | | | | | | | 3 | | | | 2 |
| Panthenol | | | | | | 1.0 | | | | | |
| Bisabolol | | | | | | 0.2 | | | | | |
| Tocopherol/Tocopherylacetate | | | | | | 1.0 | | | | | |
| Magnesium sulfate × 7 water | | | | | | 1 | | | | | |
| Neo Heliopan ® Hydro (Na salt) | | 4 | | | | | 4 | | | | |
| Neo Heliopan AP (Na salt) | 2 | | | 1 | 2 | | 1 | | | | |
| Neo Heliopan ® 303 | 6 | 2 | | | | | | | 6 | | |
| Neo Heliopan ® BB | | 2 | | 2 | | 2 | | | | | |
| Neo Heliopan ® MBC | 2 | | | | 3 | | 4 | | 2 | | |
| Neo Heliopan ® OS | | | | | 10 | | 8 | | | | |
| Neo Heliopan ® E 1000 | | | 5 | 6 | | | | | | 5 | |
| Neo Heliopan ® AV | | 5 | 5 | | | 7.5 | | | | 5 | |
| Uvinul ® T 150 | 1 | | | 2 | 2 | | | | 3 | 2 | |
| Parsol ® 1789 | | 1 | 1 | | | | 1 | | 0.5 | | |
| Z-Cote ® HP 1 | 4 | 10 | | | | | | 5 | | | 5 |
| Titanium dioxide T 805 | | | | 2 | | 3 | | 7 | | 4 | 7 |
| Ethanol | | | | | 8 | 10 | | | | | |
| Butylene glycol | 5 | 1 | | 3 | 3 | | | | 8 | 2 | |
| Glycerin | | | 6 | 2 | | | 5 | 5 | | 3 | 5 |
| Water, preservative | | | | | | to 100, q.s. | | | | | |

TABLE 5

W/O care emulsions

| Component | 45 | 46 | 47 | 48 | 49 | 50 | 51 | 52 | 53 | 54 | 55 |
|---|---|---|---|---|---|---|---|---|---|---|---|
| L = Lotion, C = Cream | C | L | C | L | C | L | L | L | C | C | C |
| Dehymuls ® PGPH | 1 | 3 | 1 | 2 | 3 | 1 | 1 | 2 | 1 | 1 | 1 |
| Monomuls ® 90-O18 | 2 | | | | | | | 2 | | 2 | |
| Lameform ® TGI | 4 | 1 | | | 3 | | | 1 | 4 | 3 | 3 |
| Abil ® EM 90 | | | | | | 4 | | | | | |
| Isolan ® PDI | | | | | 4 | | | | | | |
| Glucate ® DO | | | 5 | | | | | | | | |
| Arlacel ® 83 | | 5 | | | | | | | | | |
| Dehymuls ® FCE | | | | | | | | | | | |
| Dehymuls ® HRE 7 | | | | | | | | 4 | 1 | | |
| Zinc stearate | 2 | 1 | | 1 | 1 | | | 1 | 1 | 1 | |
| Microcrystalline wax | | 5 | | | | 2 | | | | | 5 |
| Beeswax | 4 | | | 1 | | | | 1 | 4 | 7 | |
| Tego Care ® CG | | | | | 1 | | | | | | 0.5 |
| Prisorine ® 3505 | | | 1 | 1 | | 1 | 1 | | | | 1 |
| Dry Flo ® Plus | | | | | | | | | | | |
| SFE 839 | | | | | | | 3 | | | | |
| Emery ® 1780 | | 1 | | | | | | | | | 1 |

TABLE 5-continued

W/O care emulsions

| Component | 45 | 46 | 47 | 48 | 49 | 50 | 51 | 52 | 53 | 54 | 55 |
|---|---|---|---|---|---|---|---|---|---|---|---|
| Lanolin; anhydrous USP | | | 5 | | | | | | | 4 | |
| Oligo-α-olefin (Example 1) | 3 | 4 | 2 | 12 | 10 | 2 | 2 | 6 | 3 | 12 | 1 |
| Cegesoft ® C 17 | | | 3 | | | | | | | 1 | |
| Myritol ® PC | | | | | | 2 | | 4 | | | |
| Myritol ® 331 | | 6 | | | 2 | | 6 | 2 | | | 8 |
| Finsolv ® TN | | | | 5 | | | 2 | 5 | | | |
| Cetiol ® A | | 6 | | | | 4 | | | | | |
| Cetiol ® CC | | 8 | | | 2 | 2 | 2 | | | | 5 |
| Cetiol ® SN | | 5 | | | | | | | 3 | | |
| Cetiol ® OE | 3 | | | | 4 | | 2 | | 4 | 2 | |
| Dow Corning DC ® 345 | | | | | 1 | | 2 | | | | |
| Dow Corning DC ® 2502 | | | 1 | | 2 | | | | | | |
| Prisorine ® 3758 | | | | | 3 | | | | | | |
| Silikonöl Wacker AK ® 350 | | | | 4 | | | | 3 | | | |
| Cetiol ® 868 | | | | | | | | | | 2 | 7 |
| Cetiol ® J 600 | | | 4 | | | 2 | | | | | |
| Ceraphyl ® 45 | | | | 2 | | | | 2 | | 6 | |
| Mineral oil | | | | | 4 | | | | | | |
| Cetiol ® B | | | 2 | 4 | | | | | | 3 | |
| Eutanol ® G 16 | | 1 | | | | | | | | 3 | |
| Eutanol ® G | | | 3 | | | | | | 8 | | |
| Cetiol ® PGL | | | | | | 4 | | | 9 | | |
| Almond oil | | | | | 1 | | 5 | | | | |
| Insect Repellent ® 3535 | 2 | | | | | | | | | | |
| N,N-Diethyl-m-toluamide | | | | 3 | | | | 5 | | | |
| Photonyl ® LS | 2 | 2 | | | | | | | | | |
| Panthenol | | | | | 1.0 | | | | | | |
| Bisabolol | | | | | 0.2 | | | | | | |
| Tocopherol/Tocopheryl Acetate | | | | | 1.0 | | | | | | |
| Magnesium sulfate × 7 water | | | | | 1 | | | | | | |
| Bentone ® 38 | | | | | 1 | | | | | | |
| Propylene carbonate | | | | | 0.5 | | | | | | |
| Ethanol | | | | | | | | | | 8 | |
| Butylene Glycol | | | 2 | 6 | | | | 2 | 5 | | 2 |
| Glycerin | 5 | 3 | 3 | | 5 | 3 | 2 | | 10 | 4 | |
| Water, preservative | | | | | to 100, q.s. | | | | | | |

TABLE 6

W/O care emulsions

| Component | 56 | 57 | 58 | 59 | 60 | 61 | 62 | 63 | 64 | 65 | 66 |
|---|---|---|---|---|---|---|---|---|---|---|---|
| L = Lotion, C = Cream | L | C | L | L | C | L | L | L | L | C | C |
| Dehymuls ® PGPH | 3 | 1 | 5 | 1 | 1 | 3 | 3 | 4 | 1 | 1 | 1 |
| Monomuls ® 90-O18 | | 1 | | 1 | | | | | | | |
| Lameform ® TGI | | | | | 4 | | | 1 | | 3 | |
| Abil ® EM 90 | | | | 3 | | | | | | 2 | |
| Isolan ® PDI | | 3 | | | | | | | | | 4 |
| Glucate ® DO | 1 | | | | | | | | | | |
| Arlacel ® 83 | | | | | | 3 | | | | | |
| Dehymuls ® FCE | | | | | 4 | | 1 | | | | |
| Dehymuls ® HRE 7 | | | | | | | | | 7 | | |
| Zinc stearate | | 2 | 2 | 1 | 1 | 1 | | 1 | 1 | | 1 |
| Microcrystalline wax | | | | | 4 | | 1 | | | 4 | |
| Beeswax | | 4 | | 2 | | 2 | 1 | 1 | 2 | | 5 |
| Tego ® Care CG | | | | | | | | | | | |
| Prisorine ® 3505 | 1 | 1 | | | | | 1 | 1 | | 1 | 1 |
| Dry Flo ® Plus | 1 | | | | | | | | | | |
| SFE ® 839 | | 5 | | | 4 | | | | | | |
| Emery ® 1780 | | | | | | | | | | | |
| Lanolin anhydrous USP | | 7 | 3 | | | | | | | | |
| Oligo-α-olefin (Example 1) | 3 | 4 | 4 | 8 | 10 | 2 | 8 | 6 | 3 | 12 | 7 |
| Cegesoft ® C 17 | | 2 | | | | | | | | | |
| Myritol ® PC | | | | 8 | | | | | | | |
| Myritol ® 331 | 4 | | 3 | | 5 | 3 | | | 5 | 4 | |
| Finsolv ® TN | | | 5 | | | 7 | | | | | |
| Cetiol ® A | | | | | | | | 6 | | | |
| Cetiol ® CC | 3 | | | 6 | | 3 | | | | 8 | |
| Cetiol ® SN | | | | | 5 | | | | | | |
| Cetiol ® OE | | 3 | | 2 | | | 3 | | | | 8 |
| Dow Corning ® DC 345 | | 4 | | 2 | | 2 | | | | | |
| Dow Corning ® DC 2502 | | | | 1 | | | | | | | |

TABLE 6-continued

| W/O care emulsions | | | | | | | | | | | |
|---|---|---|---|---|---|---|---|---|---|---|---|
| Component | 56 | 57 | 58 | 59 | 60 | 61 | 62 | 63 | 64 | 65 | 66 |
| Prisorine ® 3758 | | | | | | 1 | | | | | |
| Silikonöl Wacker AK ® 350 | | | | 1 | | 1 | | 4 | | | |
| Cetiol ® 868 | | | | | | | | | | | 10 |
| Cetiol ® J 600 | 4 | | | 3 | | | | | | | |
| Ceraphyl ® 45 | | | | 1 | | | | | | 5 | 4 |
| Mineral oil | | | | | | | 9 | | | | |
| Cetiol ® B | | | | | 3 | 3 | | 2 | 2 | | |
| Eutanol ® G 16 | 1 | | | | | | | | | | |
| Eutanol ® G | | | | 2 | | | | | 5 | | |
| Cetiol ® PGL | | | 10 | | | | | 6 | | | 3 |
| Almond oil | | | 2 | | 5 | | 2 | | | | |
| Photonyl ® LS | | | | 2 | | | | | | | 2 |
| Panthenol | | | | | | 1.0 | | | | | |
| Bisabolol | | | | | | 0.2 | | | | | |
| Tocopherol/Tocopherylacetate | | | | | | 1.0 | | | | | |
| Magnesium sulfate × 7 water | | | | | | 1 | | | | | |
| Bentone ® 38 | | | | | | 1 | | | | | |
| Propylene carbonate | | | | | | 0.5 | | | | | |
| Ethanol | | | | 8 | 10 | | | | | | |
| Butylene glycol | 5 | 1 | | 3 | 3 | | | | 8 | 2 | 1 |
| Glycerin | | | 6 | 2 | | | 5 | 5 | | 3 | 5 |
| Water, preservative | | | | | | to 100, q.s. | | | | | |

TABLE 7

| O/W care emulsions | | | | | | | | | | | |
|---|---|---|---|---|---|---|---|---|---|---|---|
| Component | 67 | 68 | 69 | 70 | 71 | 72 | 73 | 74 | 75 | 76 | 77 |
| L = Lotion, C = Cream | C | C | C | L | C | L | L | C | L | C | C |
| Eumulgin ® VL 75 | | | | | | 4 | | | | | |
| Dehymuls ® PGPH | | 2 | | | | | | | | | |
| Generol ® R | | | 1 | | | | | | | | |
| Eumulgin ® B2 | | | 0.8 | | | | | | | | |
| Tween ® 60 | | | | 1 | | | | | | | |
| Cutina ® E 24 | | | 0.6 | 2 | | | | | | | |
| Hostaphat ® KL 340 N | | | | | | | | | 2 | | |
| Lanette ® E | | | | | | | | 1 | | | |
| Amphisol ® K | | 0.5 | | | | 1 | | | | 1 | 0.5 |
| Sodium stearate | | | | | 0.5 | | | | | | |
| Emulgade ® PL 68/50 | | 2.5 | | | | | | | | 4 | |
| Tego ® Care CG | | | | | | | | | | | 2 |
| Tego ® Care 450 | | | | | | | | 5 | | | |
| Cutina ® MD | | 1 | | 6 | 5 | | 4 | | | 6 | |
| Lanette ® 14 | | | | | 1 | | | 2 | | | 4 |
| Lanette ® O | 4.5 | | 4 | | 1 | 2 | | | | | 2 |
| Novata ® AB | | 1 | | | | | | | | | 1 |
| Emery ® 1780 | | | | | | 0.5 | 0.5 | | | | |
| Lanolin, anhydrous, USP | | | | | | | 5 | | | | |
| Cetiol ® SB 45 | | | 1.5 | | | | 2 | | | | |
| Oligo-α-olefin (Example 1) | 3 | 4 | 2 | 1 | 10 | 2 | 2 | 6 | 3 | 12 | 1 |
| Cegesoft ® C 17 | | | | | | | | | | | |
| Myritol ® PC | | | | | 5 | | | | | | |
| Myritol ® 331 | 2 | 5 | 5 | | | 6 | | 12 | | | |
| Finsolv ® TN | | | 2 | | | 2 | | | 8 | | 5 |
| Cetiol ® CC | 4 | 6 | | | | 4 | 4 | | | | 5 |
| Cetiol ® OE | | | | | | | | | 4 | 3 | |
| Dow Corning DC ® 245 | | | 2 | | 5 | 1 | | | | | |
| Dow Corning DC ® 2502 | | | | | 2 | 1 | | | | | |
| Prisorine ® 3758 | | | | | | 1 | | | | | |
| Silikonöl Wacker AK ® 350 | 0.5 | 0.5 | 0.5 | | | 1 | 4 | | | | |
| Cetiol ® 868 | | | | | 2 | | 4 | | | | |
| Cetiol ® J 600 | 2 | | 3 | | 3 | 2 | | | | 5 | |
| Ceraphyl ® 45 | | | | | | | 3 | | | | |
| Mineral oil | | | | 9 | | | | | | | |
| Cetiol ® SN | | | 5 | | | | | | | | |
| Cetiol ® B | | | | | | | | | | 2 | |
| Eutanol ® G | | 2 | | 3 | | | | | | | |
| Cetiol ® PGL | | | | | | | | | 5 | 5 | |
| Dry Flo ® Plus | 5 | | | | | | 1 | | | | |
| SFE 839 | 5 | | | | | | | | | | 2 |
| Almond oil | | | | | | | 1 | | | | |
| Insect Repellent ® 3535 | | 2 | 4 | | | 2 | | | | 3 | |

TABLE 7-continued

| O/W care emulsions | | | | | | | | | | | |
|---|---|---|---|---|---|---|---|---|---|---|---|
| Component | 67 | 68 | 69 | 70 | 71 | 72 | 73 | 74 | 75 | 76 | 77 |
| N,N-Diethyl-m-toluamide | | 2 | | | | | | | | 3 | |
| Photonyl ® LS | 2 | 2 | | | | 2 | | | | | |
| Panthenol | | | | | | | 1 | | | | |
| Bisabolol | | | | | | | 0.2 | | | | |
| Tocopherol/ Tocopherylacetate | | | | | | | 1 | | | | |
| Veegum ® ultra | | | | | | | | | 1 | | |
| Keltrol ® T | | | 0.4 | | | | | | 0.5 | | |
| Pemulen ® TR 2 | 0.3 | | | | | | | 0.3 | | | |
| Carbopol ® Ultrez 10 | | 0.3 | 0.3 | 0.2 | 0.2 | 0.2 | | | 0.1 | 0.3 | 0.2 |
| Ethanol | | | | | | | | | | 10 | |
| Butylene glycol | | | | 4 | 3 | | 2 | 5 | 2 | | |
| Glycerin | 2 | 5 | 5 | | 3 | 3 | 2 | | 4 | | 3 |
| Water, preservative, NaOH | | | | | | to 100, q.s., pH 6.5-7.5 | | | | | |

TABLE 8

| O/W care emulsions | | | | | | | | | | | |
|---|---|---|---|---|---|---|---|---|---|---|---|
| Component | 78 | 79 | 80 | 81 | 82 | 83 | 84 | 85 | 86 | 87 | 88 |
| L = Lotion, C = Cream | C | C | L | C | L | C | L | L | L | L | C |
| Eumulgin ® VL 75 | 4 | 3 | | | | | 1 | | | | 2 |
| Generol ® R | | | | | | 2 | | | | | |
| Eumulgin ® B2 | | | | | | 2 | | | | 1 | |
| Tween ® 60 | | | | | | | | | | 1 | |
| Cutina ® E 24 | | | | 2 | | | | | | | |
| Hostaphat ® KL 340 N | | | | | | | | | | | |
| Lanette ® E | 0.5 | | | | | | | | | | 1 |
| Amphisol ® K | 0.5 | 1 | | | | | 1 | 1 | | | |
| Sodium stearate | | | | | 1 | | | | | | |
| Emulgade ® PL 68/50 | | 6 | | | | | | 5 | | | 4 |
| Tego ® Care CG | | | | | | | | | | | |
| Tego ® Care 450 | | | | | | | | | 4 | | |
| Cutina ® MD | 3 | | 3 | 8 | 6 | 8 | | | | 4 | |
| Lanette ® 14 | | 2 | | | | | | 2 | | 1 | |
| Lanette ® O | 2 | | | 2 | | 3 | 1 | | 1 | 1 | 6 |
| Novata ® AB | | | | | | | | | | | |
| Emery ® 1780 | | | | | | | | | | | |
| Lanolin, anhydrous, USP | | | | | | 4 | | | | | |
| Cetiol ® SB 45 | | | | | | | 2 | | | | |
| Oligo-α-olefin (Example 1) | 3 | 4 | 2 | 1 | 10 | 2 | 2 | 6 | 3 | 12 | 1 |
| Cegesoft ® C 17 | 4 | | | | | | | | | | |
| Myritol ® PC | 6 | | | | 5 | | | 5 | | | |
| Myritol ® 331 | 5 | | 5 | | | | 7 | | 3 | 10 | 3 |
| Finsolv ® TN | | 5 | | | 5 | | | 3 | 3 | | 1 |
| Cetiol ® CC | | | | | | | | | | | 2 |
| Cetiol ® OE | | | | | 2 | | 2 | 5 | | | |
| Dow Corning DC ® 245 | | 2 | | | 1 | | | | | 8 | 2 |
| Dow Corning DC ® 2502 | | 1 | | | 1 | | | | | | 3 |
| Prisorine ® 3758 | 3 | | | | | | | | | | 2 |
| Silikonöl Wacker AK ® 350 | | | | | 1 | | | | | | 1 |
| Cetiol ® 868 | | 2 | | | | | | | | | |
| Cetiol ® J 600 | | 2 | | | | | | | | | |
| Ceraphyl ® 45 | | | | | | | 3 | | | | |
| Cetiol ® SN | | | | | | | | | | | |
| Cetiol ® B | | | 5 | | 5 | | 4 | | | 3 | |
| Eutanol ® G | | 3 | 5 | | 5 | | | | | | |
| Cetiol ® PGL | | | | | | | | 5 | 2 | | |
| Dry Flo ® Plus | | 1 | | | | | | | | 1 | |
| SFE 839 | 1 | 1 | | | | | | | | | |
| Almond oil | | | | | | 2 | | | | | |
| Photonyl ® LS | | | | | | 2 | | | | | |
| Panthenol | | | | | | | 1 | | | | |
| Bisabolol | | | | | | | 0.2 | | | | |
| Tocopherol/ Tocopherylacetate | | | | | | | 1 | | | | |
| Veegum ® Ultra | | | | | | | | | 1 | | |
| Keltrol ® T | | | | | | | | | 0.5 | | |
| Carbopol ® ETD 2001 | | 0.3 | | 0.3 | | 0.5 | 0.2 | 0.2 | | | |
| Pemulen ® TR 2 | | | 0.3 | | 0.3 | | | | | | 0.5 |

TABLE 8-continued

| O/W care emulsions | | | | | | | | | | | |
|---|---|---|---|---|---|---|---|---|---|---|---|
| Component | 78 | 79 | 80 | 81 | 82 | 83 | 84 | 85 | 86 | 87 | 88 |
| Ethanol | | 5 | | 8 | | | | | | | 10 |
| Butylene glycol | 5 | | 2 | 3 | 3 | | | | | 8 | |
| Glycerin | 2 | 4 | 3 | 3 | | 7 | 5 | 3 | 5 | | |
| Water, preservative, | | | | | to 100, q.s. | | | | | | |
| NaOH | | | | | (pH 6.5-7.5) | | | | | | |

TABLE 9

| Spray formulations | | | | | | | | | | | |
|---|---|---|---|---|---|---|---|---|---|---|---|
| Component | 89 | 90 | 91 | 92 | 93 | 94 | 95 | 96 | 97 | 98 | 99 |
| S = Body spray, S* = Sun protection spray | S | S | S | S | S | S* | S* | S* | S* | S* | S* |
| Emulgade ® SE-PF | 8.9 | | 7.5 | 7.5 | 4.3 | 9.8 | 8.2 | 9.9 | | | |
| Eumulgin ® B2 | 3.1 | | 3 | | | | | 4.2 | | | |
| Eumulgin ® B3 | | | | | | 4.2 | 3.3 | | | | |
| Eumulgin ® HRE 40 | | | | | 4.7 | | | | | | |
| Cutina ® E 24 | | 5.9 | | 4 | | | | | | | |
| Amphisol ® K | | | | | | | | | 1 | 1 | 1 |
| Eumulgin ® VL 75 | | | | | | | | | | | 2 |
| Emulgade ® PL 68/50 | | 0.5 | | | | | | | 2.5 | 1 | |
| Cutina ® MD | | 3.1 | | | | | | | | | |
| Antaron V 220 | | | | | | 1 | 1 | 1 | | 1 | 1 |
| Oligo-α-olefin (Example 1) | 11 | 5 | 7 | 7 | 7 | 5 | 4 | 5 | 5 | 4 | 6 |
| Myritol ® PC | | | | | | | | | | | |
| Myritol ® 331 | | | 3 | 4 | 3 | 3 | 3 | 3 | | | |
| Finsolv ® TN | | 4 | | | | | 8 | | | | |
| Cetiol ® CC | 6 | | | 5 | 5 | 2 | 2 | 4 | | | |
| Cetiol ® OE | | 5 | 5 | | | 2 | | | | | |
| Dow Corning DC ® 345 | | 4 | 4 | 5 | | | | | | | |
| Cetiol ® 868 | 3 | | | | | | | | | | |
| Cetiol ® J 600 | | | 2 | 2 | | | | | | | |
| Mineral oil | | | 2 | | | | | | | | |
| Cetiol ® B | | | | | | | 2 | | | | |
| Eutanol ® G | 2 | | | 1 | | | | | | | |
| Photonyl ® LS | 2 | | | | | | 2 | | | 2 | 2 |
| Panthenol | | | | | | 1 | | | | | |
| Bisabolol | | | | | | 0.2 | | | | | |
| Tocopherol/ Tocopherylacetate | | | | | | 1 | | | | | |
| Neo Heliopan ® Hydro (Na salt) | | | | | | 2 | | | 3 | | |
| Neo Heliopan AP (Na salt) | | | | | | 2 | 2 | 2 | | | 1 |
| Eusolex ® OCR | | | | | | | 2 | | | | 3 |
| Neo Heliopan ® BB | | | | | | | | | | 1 | |
| Neo Heliopan ® MBC | | | | | | 2 | 2 | 2 | | 1 | 1 |
| Neo Heliopan ® OS | | | | | | 5 | | | | | |
| Neo Heliopan ® AV | | | | | | 6 | 6 | 2 | | 7.5 | 2 |
| Uvinul ® T 150 | | | | | | 1 | 1 | 1 | | 1 | |
| Parsol ® 1789 | | | | | | 1 | | 1 | | 1 | |
| Z-Cote ® HP 1 | | | | | | | | | | 2 | 2 |
| Eusolex ® T 2000 | | | | | | | | | | 2 | 2 |
| Veegum ® Ultra | | | | | | | | | | | 1.5 |
| Laponite ® XLG | | | | | | | | | | 1.5 | |
| Keltrol ® T | | | | | | | | | | | 0.5 |
| Pemulen ® TR 2 | | | | | | | | | 0.2 | | |
| Insect Repellent ® 3535 | 1 | | | | | | | | | | |
| N,N-Diethyl-m-toluamide | 1 | | | | | | | | | | |
| Ethanol | | | | | | | | | | | |
| Butylene glycol | | | | | | | 1 | | | 2 | 1 |
| Glycerin | | | | | | 3 | 2 | 3 | 2 | | 3 |
| Water/preservative/ NaOH | | | | | to 100/q.s./q.s | | | | | | |

TABLE 10

Antiperspirant/deodorant formulations

| Component | 100 | 101 | 102 | 103 | 104 | 105 | 106 | 107 | 108 | 109 | 110 |
|---|---|---|---|---|---|---|---|---|---|---|---|
| S = stick; SO = soft solid; RA = roll-on, anhydrous; A = aerosol; RH = Roll-on, hydrous; C = cream | S | S | SO | SO | RA | RA | A | A | RH | RH | C |
| Lanette ® 18 | 14.7 | 14.7 | | | | | | | | | |
| Cutina ® HR | 3.7 | 3.7 | 6.5 | 6.5 | | | | | | | |
| Emulgade ® NLB | | | | | | | | | 5.0 | | |
| Eumulgin ® S2 | | | | | | | | | | 3.0 | |
| Eumulgin ® S21 | | | | | | | | | | 2.5 | |
| Eumugade ® SE | | | | | | | | | | | 6.0 |
| Lanette ® 22 | | | | | | | | | | | 2.0 |
| Novata ® B | | | 10.0 | 10.0 | | | | | | | |
| Dow Corning ® DC 245 | | 15.0 | 14.0 | | 20.0 | 10.0 | | | | | |
| Cetiol ® OE | | | 9.0 | 9.0 | 5.0 | 5.0 | 5.0 | | | | 3.0 |
| Cetiol ® S | | 14.7 | 14.0 | 10.0 | 5.0 | | | | | | |
| Finsolv ® TN | | | | | | 10.0 | | | | | |
| Cetiol ® CC | | | | | | | 3.0 | | 4.0 | 2.0 | |
| Eutanol ® G16 | | 5.0 | | | | 10.0 | | | | | |
| Oligo-α-olefin (Example | 58.7 | 15.0 | 15.0 | 37.0 | 40.0 | 35.0 | 10.0 | 13.0 | 2.0 | 4.0 | 6.0 |
| Dow Corning ® DC 200 | | | | | | | | | 1.0 | 1.0 | 1.0 |
| Miglyol ® Gel B | | | 0.5 | 0.5 | 1.5 | 1.5 | 4.0 | 4.0 | | | |
| Bentone ® 38 | | | 1.0 | 1.0 | 4.5 | 4.5 | | | | | |
| Talcum | | | 5.0 | 5.0 | | | | | | | |
| Rezal ® 36 GP | 22.9 | | 25.0 | | 24.0 | | | | | | |
| Rezal ® 36 GC | | | | | | | | | | | 30.0 |
| Locron ® P | | 22.9 | | 25.0 | | 24.0 | 6.0 | 8.0 | | | |
| Locron ® L | | | | | | | | | 40.0 | 40.0 | |
| Hydagen ® CAT | | | | | | | 2.0 | | | | |
| Hydagen ® DCMF | | | | | | | | | | | 0.05 |
| Propellant gas | | | | | | | 75.0 | 75.0 | | | |
| Water | | | | | | | | | 48.0 | 47.5 | 51.9 |
| Preservative | qs | qs | qs | qs | qs | qs | qs | qs | qs | qs | qs |

APPENDIX

1) Abil ® EM 90
INCI: Cetyl Dimethicone Copolyol
Manufacturer: Tego Cosmetics (Goldschmidt)
2) Amphisol ® K
INCI: Potassium Cetyl Phosphate
Manufacturer: Hoffmann La Roche
3) Antaron ® V 220
INCI: PVP/Eicosene Copolymer
Manufacturer: GAF General Aniline Firm Corp. (IPS-Global)
4) Antaron ® V 216
INCI: PVP/Hexadecene Copolymer
Manufacturer: GAF General Aniline Firm Corp. (IPS-Global)
5) Arlacel ® 83
INCI: Sorbitan Sesquioleate
Manufacturer: Uniqema (ICI Surfacants)
6) Arlacel ® P 135
INCI: PEG-30 Dipolyhydroxystearate
Manufacturer: Uniqema (ICI Surfacants)
7) Bentone ® 38
INCI: Quaternium-18 Hectorite
Manufacturer: Rheox (Elementis Specialties)
8) Carbopol ® 980
INCI: Carbomer
Manufacturer: Goodrich
9) Carbopol ® 2984
INCI: Carbomer
Manufacturer: Goodrich
10) Carbopol ® ETD 2001
INCI: Carbomer
Manufacturer: B F Goodrich

APPENDIX

11) Carbopol ® Ultrez 10
INCI: Carbomer
Manufacturer: Goodrich
12) Cegesoft ® C 17
INCI: Myristyl Lactate
Manufacturer: Cognis Deutschland GmbH, Grünau
13) Ceraphyl ® 45
INCI: Diethylhexyl Malate
Manufacturer: International Specialty Products
14) Cetiol ® 868
INCI: Ethylhexyl Stearate
Manufacturer: Cognis Deutschland GmbH
15) Cetiol ® A
INCI: Hexyl Laurate
Manufacturer: Cognis Deutschland GmbH
16) Cetiol ® B
INCI: Butyl Adipate
Manufacturer: Cognis Deutschland GmbH (Henkel)
17) Cetiol ® J 600
INCI: Oleyl Erucate
Manufacturer: Cognis Deutschland GmbH
18) Cetiol ® OE
INCI: Dicaprylyl Ether
Manufacturer: Cognis Deutschland GmbH
19) Cetiol ® PGL
INCI: Hexyldecanol, Hexyldecyl Laurate
Manufacturer: Cognis Deutschland GmbH
20) Cetiol ® CC
INCI: Dicaprylyl Carbonate
Manufacturer: Cognis Deutschland GmbH
21) Cetiol ® SB 45
INCI: Shea Butter Butyrospermum Parkii (Linne)

APPENDIX

Manufacturer: Cognis Deutschland GmbH
22) Cetiol ® SN
INCI: Cetearyl Isononanoate
Manufacturer: Cognis Deutschland GmbH (Henkel)
23) Cutina ® E24
INCI: PEG-20 Glyceryl Stearate
Manufacturer: Cognis Deutschland GmbH
24) Cutina ® MD
INCI: Glyceryl Stearate
Manufacturer: Cognis Deutschland GmbH
25) Dehymuls ® FCE
INCI: Dicocoyl Pentaerythrityl Distearyl Citrate
Manufacturer: Cognis Deutschland GmbH
26) Dehymuls ® HRE 7
INCI: PEG-7 Hydrogenated Castor Oil
Manufacturer: Cognis Deutschland GmbH
27) Dehymuls ® PGPH
INCI: Polyglyceryl-2 Dipolyhydroxystearate
Manufacturer: Cognis Deutschland GmbH
28) Dow Corning ® 345 Fluid
INCI: Cyclomethicone
Manufacturer: Dow Corning
29) Dow Corning ® 245 Fluid
INCI: Cyclopentasiloxane Cyclomethicone
Manufacturer: Dow Corning
30) Dow Corning ® 2502
INCI: Cetyl Dimethicone
Manufacturer: Dow Corning
31) Dry ® Flo Plus
INCI: Aluminium Starch Octenylsuccinate
Manufacturer: National Starch
32) Elfacos ®ST 37
INCI: PEG-22 Dodecyl Glycol Copolymer
Manufacturer: Akzo-Nobel
33) Elfacos ®ST 9
INCI: PEG-45 Dodecyl Glycol Copolymer
Manufacturer: Akzo-Nobel
34) Emery ® 1780
INCI: Lanolin Alcohol
Manufacturer: Cognis Corporation (Emery)
35) Emulgade ® PL 68/50
INCI: Cetearyl Glucoside, Ceteayl Alcohol
Manufacturer: Cognis Deutschland GmbH
36) Emulgade ® SE-PF
INCI: Glyceryl Stearate, Ceteareth-20, Ceteareth-12, Cetearyl Alcohol, Cetyl Palmitate
Manufacturer: Cognis Deutschland GmbH
37) Eumulgin ® B 2
INCI: Ceteareth-20
Manufacturer: Cognis Deutschland GmbH
38) Eumulgin ® VL 75
INCI: Lauryl Glucoside (and) Polyglyceryl-2 Dipolyhydroxystearate (and) Glycerin
Manufacturer: Cognis Deutschland GmbH
39) Eusolex ® OCR
INCI: Octocrylene
Manufacturer: Merck
40) Eusolex ®T 2000
INCI: Titanium Dioxide, Alumina, Simethicone
Manufacturer: Rona (Merck)
41) Eutanol ® G
INCI: Octyldodecanol
Manufacturer: Cognis Deutschland GmbH
42) Eutanol ®G 16
INCI: Hexyldecanol
Manufacturer: Cognis Deutschland GmbH
43) Eutanol ®G 16 S
INCI: Hexyldecyl Stearate
Manufacturer: Cognis Deutschland GmbH
44) Finsolv ® TN
INCI: C 12/15 Alkyl Benzoate
Manufacturer: Findex (Nordmann/Rassmann)
45) General ® R
INCI: *Brassica Campestris* (Rapseed) Sterols
Manufacturer: Cognis Deutschland GmbH
46) Glucate ® DO
INCI: Methyl Glucose Dioleate
Manufacturer: NRC Nordmann/Rassmann
47) Hostaphat ® KL 340 N
INCI: Trilaureth -4 Phosphate
Manufacturer: Clariant
48) Isolan ® PDI
INCI: Diisostearoyl Polyglyceryl-3 Diisostearate
Manufacturer: Goldschmidt AG
49) Keltrol ® T
INCI: Xanthan Gum
Manufacturer: CP Kelco
50) Lameform ® TGI
INCI: Polyglyceryl-3 Diisostearate
Manufacturer: Cognis Deutschland GmbH
50) Lanette ® 14
INCI: Myristyl Alcohol
Manufacturer: Cognis Deutschland GmbH
51) Lanette ® E
INCI: Sodium Cetearyl Sulfate
Manufacturer: Cognis Deutschland GmbH
52) Lanette ® O
INCI: Cetearyl Alcohol
Manufacturer: Cognis Deutschland GmbH
53) Monomuls ® 90-0-18
INCI: Glyceryl Oleate
Manufacturer: Cognis Deutschland GmbH
54) Myrj ® 51
INCI: PEG-30-Sterate
Manufacturer: Uniqema
55) Myritol ® 331
INCI: Cocoglycerides
Manufacturer: Cognis Deutschland GmbH
56) Myritol ® PC
INCI: Propylene Glycol Dicaprylate/Dicaprate
Manufacturer: Cognis Deutschland GmbH
57) Neo Heliopan ® 303
INCI: Octocrylene
Manufacturer: Haarmann & Reimer
58) Neo Heliopan ® AP
INCI: Disodium Phenyl Dibenzimidazole Tetrasulfonate
Manufacturer: Haarmann & Reimer
59) Neo Heliopan ® AV
INCI: Ethylhexyl Methoxycinnamate
Manufacturer: Haarmann & Reimer
60) Neo Heliopan ® BB
INCI: Benzophenone-3
Manufacturer: Haarmann & Reimer
61) Neo Heliopan ® E 1000
INCI: Isoamyl-p-Methoxycinnamate
Manufacturer: Haarmann & Reimer
62) Neo Heliopan ® Hydro (Na-Salz)
INCI: Phenylbenzimidazole Sulfonic Acid
Manufacturer: Haarmann & Reimer
63) Neo Heliopan ® MBC
INCI: 4-Methylbenzylidene Camphor

APPENDIX

Manufacturer: Haarmann & Reimer
64) Neo Heliopan ® OS
INCI: Ethylhexyl Salicylate
Manufacturer: Haarmann & Reimer
65) Novata ® AB
INCI: Cocoglycerides
Manufacturer: Cognis Deutschland GmbH
66) Parsol ® 1789
INCI: Butyl Methoxydibenzoylmethane
Manufacturer: Hoffmann-La Roche (Givaudan)
67) Pemulen ® TR-2
INCI: Acrylates/C10-30 Alkylacrylate Crosspolymer
Manufacturer: Goodrich
68) Photonyl ® LS
INCI: Arginine, Disodium Adenosine Triphosphate, Mannitol, Pyridoxine HCL, Phenylalanine, Tyrosine
Manufacturer: Laboratoires Serobiologiques (Cognis)
69) Prisorine ® ISAC 3505
INCI: Isostearic Acid
Manufacturer: Uniqema
70) Prisorine ® 3758
INCI: Hydrogenated Polyisobutene
Manufacturer: Uniqema
71) Ravecarb ® 106
Polycarbonatdiol
Manufacturer: Enichem
73) SFE ® 839
INCI: Cyclopentasiloxane and Dimethicone/Vinyl Dimethicone Crosspolymer
Manufacturer: GE Silicones
74) Silikonöl Wacker AK ® 350
INCI: Dimethicone
Manufacturer: Wacker
75) Squatol ® S
INCI: Hydrogenated Polyisobutene
Manufacturer: LCW (7-9 rue de l'Industrie 95310 St-Ouen l'Aumone France)
76) Tego ® Care 450
INCI: Polyglyceryl-3 Methylglucose Distearate
Manufacturer: Tego Cosmetics (Goldschmidt)
77) Tego ® Care CG 90
INCI: Cetearyl Glucoside
Manufacturer: Goldschmidt
78) Tween ® 60
INCI: Polysorbate 60
Manufacturer: Uniqema (ICI Surfactants)
79) Uvinul ® T 150
INCI: Octyl Triazone
Manufacturer: BASF
80) Veegum ® Ultra
INCI: Magnesium Aluminium Silicate
Manufacturer: Vanderbilt
81) Z-Cote ® HP 1
INCI: Zinc Oxide, Dimethicone
Manufacturer: BASF

What is claimed is:

1. A body care composition comprising at least one branched oligo-α-olefin, or hydrogenated branched oligo-α-olefin, obtained by a process comprising the steps of:
   (1) oligomerizing monomers consisting of:
      (a) at least one branched α-olefin selected from the group consisting of 2-ethyl-1-hexene, 2-propyl-1-heptene, 2-methyl-1-butene, 2-methyl-1-pentene, 3-methyl-1-pentene and 4-methyl-1-pentene, or
      (b) a mixture of a branched α-olefin selected from the group consisting of 2-ethyl-1-hexene, 2-propyl-1-heptene, 2-methyl-1-butene, 2-methyl-1-pentene, 3-methyl-1-pentene and 4-methyl-1-pentene and a linear α-olefin selected from the group consisting of 1-propene, 1-butene, and 1-pentene
   in the presence of a catalyst selected from the group consisting of organic acids, cationic ion exchangers, silica gels, layer silicates, inorganic acids and Lewis-acid-based catalysts, to form a branched oligo-α-olefin, and
   (2) optionally, hydrogenating said branched oligo-α-olefin, wherein the body care composition comprises 0.1 to 100% by weight of oil components, based on the total quantity of oil components, inclusive of said at least one oligo-α-olefin or hydrogenated oligo-α-olefin, and 0.1 to 20% by weight of a surface-active substance or a mixture of surface-active substances, and the body care composition is in the form of a w/o or o/w emulsion.

2. The body care composition according to claim 1, comprising 1 to 50% by weight of oil components, based on the total quantity of oil components, inclusive of said at least one oligo-α-olefin olefin or hydrogenated oligo-α-olefin.

3. The body care composition according to claim 1, further comprising at least one antiperspirant and/or deodorant active principle.

* * * * *

UNITED STATES PATENT AND TRADEMARK OFFICE
CERTIFICATE OF CORRECTION

| | | |
|---|---|---|
| PATENT NO. | : 8,715,629 B2 | Page 1 of 1 |
| APPLICATION NO. | : 10/553165 | |
| DATED | : May 6, 2014 | |
| INVENTOR(S) | : Schmid et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2518 days.

Signed and Sealed this
Eleventh Day of August, 2015

Michelle K. Lee
*Director of the United States Patent and Trademark Office*